United States Patent [19]

Hussmann et al.

[11] Patent Number: 4,783,569

[45] Date of Patent: Nov. 8, 1988

[54] SELECTIVE GAS-PHASE ISOMERIZATION OF DIMETHYLNAPHTHALENE: 2,6-DMN TRIAD

[75] Inventors: Gregory P. Hussmann, Batavia; Patrick E. Mc Mahon, Wheaton, both of Ill.

[73] Assignee: Amoco Corporation, Chicago, Ill.

[21] Appl. No.: 53,796

[22] Filed: May 26, 1987

[51] Int. Cl.[4] ............................................. C07C 5/22
[52] U.S. Cl. .................................................... 585/481
[58] Field of Search ........................................ 585/481

[56] References Cited

U.S. PATENT DOCUMENTS

| | | | |
|---|---|---|---|
| 3,888,938 | 6/1975 | Ogasawara et al. | 585/481 |
| 4,041,089 | 8/1977 | Allen et al. | 585/481 |
| 4,556,751 | 12/1985 | Maki et al. | 585/481 |

Primary Examiner—Curtis R. Davis
Attorney, Agent, or Firm—Reed F. Riley; William H. Magidson; Ralph C. Medhurst

[57] ABSTRACT

A gas-phase isomerization process wherein a feed containing one or more members of the 2,6-DMN isomer triad is selectively isomerized over a lower-acidity, supported, molecular-sieve-based catalyst composition to form essentially thermodynamic equilibrium amounts of the members of the 2,6-triad and reduced amounts of outside-the-triad products.

12 Claims, No Drawings

SELECTIVE GAS-PHASE ISOMERIZATION OF DIMETHYLNAPHTHALENE: 2,6-DMN TRIAD

BACKGROUND OF THE INVENTION

This invention relates to a process for catalytically isomerizing 1,5-dimethylnaphthalene (1,5-DMN), 1,6-dimethylnaphthalene (1,6-DMN), 2,6-dimethylnaphthalene (2,6-DMN), or some mixture thereof, at an elevated temperature in the gas-phase selectively to a mixture of 1,5-DMN, 1,6-DMN, and 2,6-DMN (the 2,6-DMN triad) in which the amount of each of the 2,6-DMN triad isomers closely approximates the equilibrium concentration calculated for the temperature at which the isomerization is carried out, and production of outside-the-2,6-DMN-triad products is minimized. More particularly, this invention relates to an elevated temperature, molecular-sieve-catalyst-composition catalyzed, gas-phase isomerization process wherein a feed containing one or more of the 2,6-DMN triad isomers is isomerized over a lower acidity, molecular-sieve-based catalyst composition to a reaction product containing essentially 2,6-DMN triad isomers and wherein the amounts of the respective 2,6-DMN triad isomers in the reaction product are close to their equilibrium values calculated for the temperature of isomerization.

The ten isomers of dimethylnaphthalene can be conveniently divided into four groups when discussing isomerization. These are the 2,6-DMN triad (1,5-DMN; 1,6-DMN; 2,6-DMN), the 2,7-DMN triad (2,7-DMN; 1,7-DMN; 1,8-DMN), the 2,3-DMN triad (2,3-DMN; 1,3-DMN; 1,4-DMN), and 1,2-DMN. For various theoretical reasons, forming other members of a triad from a same-triad isomer requires less energy than forming outside-the-triad isomers. Advantage of this situation can be utilized if the appropriate isomerization catalyst can be found, since commercially a single isomer of DMN is often required in high isomeric purity. For example, one method of preparation of 2,6-DMN, an alkenylation process, forms 1,5-DMN as an intermediate and uses as a final step, the isomerization of 1,5-DMN to 2,6-DMN after which the 2,6-DMN is separated and the residue recycled to the isomerization step. In such a process, it is necessary to produce the 2,6-isomer with as little outside-the-triad products as possible and beneficial to reach, in each pass through the isomerization step, the equilibrium concentration of 2,6-DMN calculated for the temperature of isomerization. This insures a slow buildup of unwanted products in the recycle system and improves the per pass production of 2,6-DMN. A number of different catalysts have been suggested for the above alkenylation process isomerization step, but no one is completely satisfactory in that either too much outside-the-triad products are formed per pass or near equilibrium amounts of within-the-triad isomers are not formed.

A substantial literature exists for the isomerization of DMN and within it attention has been given to isomerization of both pure DMN isomers and DMN isomer mixtures. Attention has also been directed to carrying out the isomerization in both gas and liquid phases. An example of a study of the liquid-phase isomerization of DMN is found in *J. Org. Chem.* 29, 2939 (1964) where an $HF/BF_3$ mixture was used as a catalyst. Japanese Kokai No. 50-117757 (1975) teaches liquid-phase isomerization using a Y-type zeolite catalyst and claims superiority of the liquid-phase process over the gas-phase process. Gas-phase isomerization of 1,5-DMN, 1,6-DMN or a mixture of the two (isomerization within the 2,6-triad) is set forth in U.S. Pat. No. 3,798,280 wherein the catalysts taught are silica-alumina, alumina-boria or a zeolite. Isomerization of DMN to 2,6-DMN and 2,7-DMN (isomerization outside of a single triad) is taught in Ger. Offen. No. 2,243,005. The catalyst used was an alumina/silica molecular sieve. None of these processes and their attendant catalysts, particularly the ones for gas-phase isomerization within the 2,6-DMN isomer triad, are particularly satisfactory in that they do not allow rapid and essentially complete approach to the equilibrium isomer concentrations at the isomerization temperature (particularly the 2,6-DMN concentration) while simultaneously keeping the concentrations of the members of other isomer triads and cracked products at a low enough level to make the necessary recycle and 2,6-DMN separation efficient.

Now catalyst compositions have been found which are able to produce near equilibrium amounts of within-the-triad isomers at reasonable catalyst composition space velocities and also produce low amounts of outside-the-triad products, both other DMN isomers and cracked products.

SUMMARY OF THE INVENTION

Described herein is a gas-phase process to isomer at an elevated temperature a feed containing one or more members of the 2,6-DMN triad over a low-acidity, molecular-sieve-based catalyst composition to an isomerized product such that the 1,5-, 1,6-, and 2,6-DMN concentrations in said isomerized product are about their thermodynamic equilibrium values at said temperature and wherein said isomerized product contains less than about ten (10) weight percent, based upon the amount of said one or more members of the 2,6-DMN triad present in said feed, of other reaction products.

DETAILED DESCRIPTION OF THE INVENTION

The feed to the process of the instant invention contains a member of the 2,6-triad, 1,5-DMN, 1,6-DMN or 2,6-DMN. Mixtures of two or even three of the members are also useful and sometimes required. In general, the feed should not contain any appreciable amount of other DMN isomers. In a process to form 2,6-DMN from a 1,5-DMN-containing feed, the isomerized process stream from isomerization is usefully treated to separate as much of the 2,6-compound as feasible, and the 2,6-DMN lean stream recycled back to the isomerization reactor. This use necessitates some of each member of the 2,6-triad being present in the total feed to isomerization.

The feed to the isomerization unit can contain a single DMN isomer or a DMN isomer mixture, as discussed above, and is either fed neat or admixed with an inert diluent. Preferably, the feed does not include a diluent, but such diluents as hexane, toluene, benzene and the like may be used. If a diluent is used it is preferably used in an amount which is about 80 percent or less by weight of the total feed, more preferably, about 60 percent by weight or less and most preferably about 20 percent by weight or less. Inert diluents can include impurities in the DMN-containing feed.

DMNs can be formed by catalytically methylating mono-methylnaphthalene (MMN) or naphthalene (N) using methanol or dimethyl ether in an elevated-temperature, gas-phase process using for example, a fixedbed isothermal reactor. The MMN or N, diluted with an inert carrier or used neat, is combined with excess of the methylating agent and passed over a molecular sieve catalyst composition such as supported or unsupported HY, 5% Cr on HY, 5% Ni on HY, 20% Mg on HY, 15% P on HY, rare earth exchanged HY, HX, or NaX, ZSM-5, mordenite, AMS-1B (crystalline borosilicate-based molecular sieves) or Ni and Ga exchanged variants of the latter. Supports generally useful for this process are metal oxides such as alumina, silica, or silica-alumina. Greater than equilibrium amounts of the 2,6-DMN isomer in the DMN mixture can result from this process which makes such a process stream, after suitable treatment, a useful feed to the process of the instant invention.

In general the process of the instant invention can be carried out from about ambient pressure to about 1000 psi, more preferably, from about 20 psi to about 500 psi, and, most preferably, from about 50 psi to about 300 psi. The isomerization temperature is usefully held between about 250° C. and about 400° C., more preferably between about 275° C. and about 350° C., and, most preferably, between about 275° C. and about 325° C. Weight hourly space velocities useful for these isomerization reactions are usefully between about 1 and about 1000, more preferably between about 5 and about 500, and, most preferably, between about 10 and about 200. Where using the crystalline borosilicate-based catalyst compositions, the isomerization reaction temperature is preferably somewhat lower than given above and is suitably held between about 200° C. and about 350° C., more preferably, between about 250° C. and about 300° C.

A variant of the process of the instant invention can be carried out by including a small amount of a palladium-, platinum- or the like-doped, molecular-sieve-based catalyst composition to the catalyst composition employed for isomerization. A small amount of hydrogen is then added to the isomerization feed and a small amount of beneficial reduction then accompanies isomerization.

Catalyst compositions useful for the isomerization are mildly acidic, supported molecular sieves; sieves which have significant Bronsted acidity but low Lewis acidity. More particularly, they are supported crystalline borosilicate and crystalline high-$SiO_2/Al_2O_3$ ratio aluminosilicate molecular sieves. The aluminosilicate molecular sieves useful in this invention are those in which the sieve acidity is reduced by using crystalline aluminosilicates having $SiO_2/Al_2O_3$ ratios preferably greater than about 50/1 and less than about 150/1. More preferably, the $SiO_2/Al_2O$ ratio lies between about 60/1 and about 120/1. Also useful are other lower acidity crystalline molecular sieves such as supported zincosilicates, supported gallosilicates, supported scandosilicates, supported ferrisilicates and the like. More preferably, useful catalyst compositions include supported crystalline borosilicates. Useful zincosilicates are described in U.S. Ser. No. 814,646, filed 12/30/85, and useful gallosilicates are described in U.S. Ser. No. 901,613, filed 8/29/86, the contents of which applications are incorporated herein by reference. It is believed that these less acid molecular-sieve-based catalysts are primarily responsible for being able to stay within triad during isomerization yet accomplishing the isomerization with commercially acceptable efficiencies.

Supports useful generally for these molecular sieve catalyst compositions are metal oxides such as silica, alumina and silica-alumina.

The catalysts of the instant invention enable one to approach closely or actually reach the thermodynamic equilibrium amounts (measured at the isomerization temperature) of the 2,6-DMN triad isomers during isomerization. Desirably, the concentrations of each of the 2,6-DMN isomers is ninety-five (95) weight percent or greater than its equilibrium value, and, more preferably, each is essentially at or greater than its equilibrium value. Calculated equilibrium values for the 2,6-DMN triad isomers at two widely-spaced isomerization temperatures are set forth below:

| Temperature °C. | 2,6-DMN | 1,6-DMN | 1,5-DMN |
|---|---|---|---|
| | | (Weight Percent)* | |
| 327 | 37 | 47 | 15 |
| 527 | 35 | 48 | 16 |

*All calculated concentration values are about ± 10% by weight.

As may be seen, the temperature dependence of the triad concentrations is not large.

The isomerization reaction desired produces preferably less than about ten (10) weight percent outside-the-triad products, and, more preferably, less than about five (5) weight percent outside-the-triad products. Outside-the-triad products include both other DMN isomers and cracked products such as methyl naphthalene.

Some of the catalyst compositions used in this invention are based on AMS-1B crystalline borosilicate molecular sieve, which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

$0.9 \pm 0.2 M_{2/n}O:B_2O_3:ySiO_2:zH_2O$ wherein M is at least one cation, n is the oxidation state of the cation, y is between 4 and about 600 and z is between 0 and about 160.

TABLE A

| d-Spacing Å (1) | Assigned Strength (2) |
|---|---|
| 11.2 + 0.2 | W–VS |
| 10.0 + 0.2 | W–MS |
| 5.97 + 0.07 | W–M |
| 3.82 + 0.05 | VS |
| 3.70 + 0.05 | MS |
| 3.62 + 0.05 | M–MS |
| 2.97 + 0.02 | W–M |
| 1.99 + 0.02 | VW–M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reaction concentrations are indicated below:

|  | Broad | Preferred | Most Preferred |
| --- | --- | --- | --- |
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having the oxidation state n, such as an alkali or an alkaline earth metal cation or hydrogen. By regulation of the quantity of boron (represented as $B_2O_3$) in $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium lithium, calcium and magnesium. Ammonium cations may be used alone or in conjunction with such metal cations. Since basic conditions ar required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably from about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably from about 0.01 to about 0.1, more preferably from about 0.01 to about 0.1 and most preferably from about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about 1 to about 10 days and preferably is about 1 to about 7 days, at a temperature ranging from about 100° C. to about 250° C., preferably from about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about 5 to about 7 days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably from about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIA, IIIB, IVB, VB, VIB, VIIB, and VIII, and rare earth elements.

Elements of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc and cadmium. Specific combinations of nonnoble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide like alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere form a few up to 100 weight % of the total composition. Catalytic compositions can contain about 0.1 weight % to about 100 weight % crystalline borosilicate material and preferably contain about 10 weight % to about 95 weight % of such material and most preferably contain about 20 weight % to about 80 weight % of such material.

The following Examples will serve to illustrate certain specific embodiments of the herein disclosed invention. The Examples should not, however, be construed as limiting the scope of the novel invention as there are many variations which may be made thereon without departing from the spirit of the disclosed invention, as those of skill in the art will recognize.

EXAMPLES

General

To carry out the isomerization reactions in the Examples below, a 5 or 10 ml portion of a catalyst composition (14/42 mesh) was charged into a small glass reactor. The feed, 10 weight percent 1,5-DMN in toluene, was added at 0.1 g/min. A nitrogen carrier gas was used to sweep the feed through the reactor. The effluent was collected in an ice-cooled receiver and analyzed by gas chromatography. All percents are given in weight percent.

EXAMPLE 1

| 1,5-DMN Isomerization With A HAMS-1B Catalyst Composition[1,2] | | | | | | |
|---|---|---|---|---|---|---|
| Liquid Feed Rate[3] (cc/hr) | Temp. (°C.) | % GC Area (Normalized)[4] | | | | |
| | | 2,6-DMN | 1,6-DMN | 1,5-DMN | 2,7-DMN | 1,7-DMN | Me-Naph |
| 2.3 | 275 | 46 | 40 | 6.0 | 2.0 | 1.0 | 5 |
| 3.1 | 275 | 43 | 39 | 8.0 | 1.0 | 2.0 | 7 |
| 4.4 | 275 | 43 | 38 | 9.8 | 1.0 | 1.0 | 6 |
| 2.3 | 300 | 42 | 35 | 5.3 | 1.8 | 3.5 | 12 |

[1]A 10 ml portion of each catalyst composition was used.
[2]Sieve made according to European Patent No. 68796, Example 8. Catalyst composition is 40% sieve and 60% $\gamma$-Al$_2$O$_3$.
[3]Feed was 10 weight percent 1,5-DMN in benzene.
[4]Accuracy of the concentrations is about ± 1 weight percent.

EXAMPLE 2

| 1,5-DMN Isomerization With Aluminosilicate Catalysts[1,2,3] | | | | | | |
|---|---|---|---|---|---|---|
| Catalyst Example No./ (SiO$_2$/Al$_2$O$_3$) | Temp. (°C.) | % GC Area (Normalized)[5] | | | | |
| | | 2,6-DMN | 1,6-DMN | 1,5-DMN | 2,7-DMN | Me-Naph |
| Comparative[4] Example 3 (30:1) | 325 | 23.8 | 24.5 | 4.5 | 10.9 | 5.4 |
| Example 4 | 300 | 23.8 | 35.1 | 37.6 | — | — |

-continued 1,5-DMN Isomerization With Aluminosilicate Catalysts[1,2,3]

| Catalyst Example No./($SiO_2/Al_2O_3$) | Temp. (°C.) | % GC Area (Normalized)[5] | | | | |
|---|---|---|---|---|---|---|
| | | 2,6-DMN | 1,6-DMN | 1,5-DMN | 2,7-DMN | Me-Naph |
| Example 4 (60:1) | 325 | 39.9 | 43.2 | 15.3 | >2 | — |
| Example 4 (60:1) | 350 | 39.2 | 42.9 | 8.1 | 7.0 | — |
| Example 4 (60:1) | 375 | 33.5 | 44.0 | — | 12.4 | 4.9 |
| Example 5 (120:1) | 325 | 34.6 | 43.1 | 22.3 | — | — |

[1] A 5 ml portion of each catalyst composition was used.
[2] A liquid feed rate of 0.1 g/min. of a 10 weight percent solution of 1,5-DMN in toluene was used.
[3] Aluminosilicates used were of the pentasil structure as determined by XRD.
[4] 8.0% 1,7-DMN was coproduced.
[5] Accuracy of the concentrations is about ± 1 weight percent.

COMPARATIVE EXAMPLE 3

Sieve Preparation

The sieve of this Example was a composite of five preparations each of which was prepared in an identical fashion and set forth below.

A 207 g portion of tetrapropyl ammonium bromide and a 42 g portion of sodium aluminate were dissolved in a solution containing 37 g of sodium hydroxide and 400 cc of distilled water. Then, 1077 g Ludox AA 40 made by E. I. DuPont & Co. was added with enough distilled water to make a total volume of 1800 ml. The mixture was stirred over low heat for 10 minutes and autoclaved at 150° C. at autogenous pressure for 6 days. The solid product was separated by filtration, washed three times with hot distilled water, dried overnight at 120° C. and calcined for 3 hrs at 538° C. The product was exchanged with an equal weight of ammonium nitrate dissolved in enough distilled water to make a 15% by weight solution. The exchange was carried out a total of three times by stirring for 1 hr at 820° C., filtering and reslurrying. The product was then washed with hot distilled water three times and dried at 120° C. Analysis of the sieve showed:
Crystallinity: 87%–91% (X-ray)
Sodium: 6–32 ppm
$SiO_2$: 84.5%–86.2%
$Al_2O_3$: 2.93%–3.92%

Catalyst Composition Preparation

A 692 g portion of a mixture of the five preparations above was mixed with 103 g of PHF alumina powder made by American Cyanamid Co., 43 g of Sterotex extrusion aid and 690 g of PHF alumina sol (9.45% alumina) and extruded after mulling. The extrudate was dried at 120° C., calcined for 2 hrs at 260° C., 2 hrs at 400° C. and 3 hrs at 538° C. The resulting catalyst composition contained 80% sieve and 20% $\gamma$-$Al_2O_3$.

EXAMPLE 4

Sieve Preparation

The preparative procedure was the same as used in Example 3 except 23.7 g sodium aluminate was used and the procedure carried out but once. Analysis of the sieve showed:
Crystallinity: 81% (X-ray)
Sodium: 7 ppm
$SiO_2$: 94.4%
$Al_2O_3$: 2.45%

Catalyst Composition Preparation

A 90.00 g portion of the sieve was composited with 106 g of PHF alumina (9.45% alumina) and enough water to make thick paste. It was dried overnight at 120° C. and calcined at 538° C. for 4 hrs. The resulting catalyst composition contained 90% sieve and 10% $\gamma$-$Al_2O_3$.

EXAMPLE 5

Sieve Preparation

The preparative procedure was the same as used in Example 3 except that 11.1 g of sodium aluminate was used and the procedure carried out but once. Analysis of the sieve showed:
Crystallinity: 80%–84% (X-ray)
Sodium: 15 ppm
$SiO_2$: 87.15%
$Al_2O_3$: 1.30%

Catalyst Composition Preparation

A 90.00 g portion of the sieve was composited with 106 g of PHF alumina sol (9.45% alumina). It was dried overnight at 120° C. It was then calcined at 538° C. for 4 hrs and pelletized, dried overnight at 120° C. again and calcined at 538° C. for 4 hrs. The resulting catalyst composition contained 90% sieve and 10% $\gamma$-$Al_2O_3$.

What is claimed is:

1. A gas-phase process to isomerize at an elevated temperature a feed containing one or more members of the 2,6-DMN triad over a catalyst composition comprising a supported crystalline borosilicate molecular sieve or a supported crystalline aluminosilicate molecular sieve, said aluminosilicate molecular sieve having a silica/alumina ratio of between about 50/1 and about 150/1, to an isomerized product such that each of the 1,5-, 1,6- and 2,6-DMN concentrations in said isomerized product is about its thermodynamic equilibrium value at said temperature, and wherein said isomerized product contains less than about ten (10) weight percent, based upon the amount of said one or more members of the 2,6-DMN triad present in said feed, of other reaction products.

2. The process of claim 1 wherein said other reaction products in said isomerized product constitute less than about five (5) weight percent of the amount of said one or more members of the 2,6-DMN triad in said feed.

3. The process of claim 1 wherein said temperature of isomerization lies between about 250° C. and about 400° C.

4. The process of claim 2 wherein said temperature of isomerization lies between about 250° C. and about 400° C.

5. The process of claim 3 wherein said isomerized product is treated to separate 2,6-DMN to form a 2,6-DMN rich stream and a 2,6-DMN poor stream, said 2,6-DMN poor stream being recycled to said gas-phase process.

6. The process of claim 4 wherein said isomerized product is treated to separate 2,6-DMN to form a 2,6-DMN rich stream and a 2,6-DMN poor stream, said 2,6-DMN poor stream being recycled to said gas-phase process.

7. The process of claim 2 wherein said catalyst composition comprises a supported crystalline borosilicate molecular sieve.

8. The process of claim 2 wherein said catalyst composition comprises a supported crystalline aluminosilicate molecular sieve having a silica/alumina ratio of between about 50/1 and about 150/1.

9. The process of claim 7 wherein said temperature of isomerization lies between about 200° C. and about 300° C.

10. The process of claim 8 wherein said temperature of isomerization lies between about 275° C. and about 350° C.

11. The process of claim 9 wherein said isomerized product is treated to separate 2,6-DMN to form a 2,6-DMN rich stream and a 2,6-DMN poor stream, said 2,6-DMN poor stream being recycled to said gas-phase process.

12. The process of claim 10 wherein said isomerized product is treated to separate 2,6-DMN to form a 2,6-DMN rich stream and a 2,6-DMN poor stream, s aid 2,6-DMN poor stream being recycled to said gas-phase process.

* * * * *